(12) United States Patent
Tian et al.

(10) Patent No.: US 6,716,431 B1
(45) Date of Patent: Apr. 6, 2004

(54) DIFFERENTIAL CYTOTOXICITY OF ALTERNATIVE FORMS OF ROTAVIRUS NONSTRUCTURAL PROTEIN 4

(75) Inventors: Peng Tian, Monroe, NY (US); Timothy J. Zamb, Nyack, NY (US); Stephen A. Udem, New York, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/048,540

(22) PCT Filed: May 28, 1999

(86) PCT No.: PCT/US99/11872

§ 371 (c)(1),
(2), (4) Date: Dec. 7, 2001

(87) PCT Pub. No.: WO99/61621

PCT Pub. Date: Dec. 2, 1999

Related U.S. Application Data

(60) Provisional application No. 60/087,320, filed on May 29, 1998.

(51) Int. Cl.[7] .......................... A61K 39/15; C12N 7/01; C12N 15/46; C12N 15/63
(52) U.S. Cl. .................. 424/215.1; 435/235.1; 435/236; 435/320.1; 435/69.3; 536/23.72
(58) Field of Search .............................. 435/235.1, 236, 435/252.3, 325, 69.1, 69.3; 424/215.1; 536/23.72

(56) References Cited

PUBLICATIONS

Ciarlet et al. Archives of Virology 145:371–383, 2000.*
Cunliffe et al. Journal of Medical Virology 53:41–50, Sep. 1997.*
Horie et al. Archives of Virology 142:1865–1872, Sep. 1997.*

* cited by examiner

*Primary Examiner*—Mary Mosher
(74) *Attorney, Agent, or Firm*—J. Darrell Fontenot (57) ABSTRACT

The nonstructural protein 4 (NSP4) in the SA11 ATCC rotavirus strain has a histidine at amino acid position 47. This substituted form is more cytotoxic than the NSP4 of the Australia rotavirus strain, which has an asparagine at amino acid position 47. The histidine at amino acid position 47 is mutagenized to another amino acid to produce an alternative form of NSP4 which has reduced toxicity, while retaining its antigenicity and immunogenicity. NSP4 having a glutamic acid at amino acid position 48 is more cytotoxic than NSP4 having a lysine at amino acid position 48. The lysine at amino acid position 48 is mutagenized to another amino acid other than glutamic acid to produce an alternative form of NSP4 which has reduced toxicity, while retaining its antigenicity and immunogenicity.

17 Claims, 6 Drawing Sheets

DIFFERENTIAL CYTOTOXICITY OF ALTERNATIVE FORMS OF ROTAVIRUS NONSTRUCTURAL PROTEIN 4

This application claims the benefit of provisional application No. 60/087,320, filed May 29, 1998.

FIELD OF THE INVENTION

This invention relates to the identification of sequence differences in alternative forms of rotavirus nonstructural protein 4 which result in significant changes in cytotoxicity.

BACKGROUND OF THE INVENTION

Rotaviruses are recognized as the most important cause of severe viral gastroenteritis in humans and animals (Bibliography entry 1). Rotaviruses are non-enveloped, triple-layered particles with a genome consisting of 11 segments of double-stranded RNA. Group A rotaviruses are the major cause of rotaviral disease in humans and animals.

The prototypic Group A rotavirus, designated SA11, was discovered 10 years before human rotaviruses were identified. Malherbe et al. (2) described the isolation of a virus, simian agent 11 (SA11), from the rectum of a healthy vervet monkey and its cytopathic effects in vervet monkey kidney call cultures. The virus was distributed to Holmes et al. (Dept. Microbiology, University of Melbourne, Australia) (3), Estes et al. (Division of Molecular Virology, Baylor College of Medicine, Houston, Tex., USA) (4), and the American Type Culture Collection. Unfortunately, the precise passage history of each virus sample is not known.

The nonstructural protein 4, referred to as NSP4, is encoded by gene 10 of group A rotaviruses. Among the several putative roles of the multifunctional rotavirus nonstructural protein 4 (NSP4) is disease pathogenesis (5–11). That contention is based on several past studies of the NSP4 encoded by the prototypic rotavirus, strain SA11 (5–8).

The nucleotide sequence of gene 10 from the SA11 strain of rotavirus, a prototype of group A rotavirus, was reported by Both et al. in 1983 based on analysis of a plaque purified virus stock from Australia provided by Holmes et al. (12). The sequencing was performed by a combination of methods. Parts of the gene 10 were subcloned into bacteriophage M13 and sequenced by the Sanger method (13); other regions of the cDNA clone were sequenced by the method of Maxam and Gilbert (14).

Previous studies of NSP4 (5–8,11,12,15–23) are based upon a cDNA clone of this version of the NSP4 gene provided by Both et al. The original NSP4 sequence of the Australian strain has an asparagine at amino acid position 47 (NSP4 (Asn)) (12) in the deduced amino acid sequence.

NSP4 is a transmembrane protein with multiple functions. It acts as an intracellular receptor for subviral particles budding into the endoplasmic reticulum (ER) of infected cells (16,21). The expression of NSP4 results in increased intracellular calcium levels ($[Ca^{2+}]_i$) in Sf9 insect cells (5). Similar effects on intracellular calcium changes were observed with NSP4 from the OSU strain, a different group A rotavirus (9). A phospholipase C (PLC) mediated pathway is activated when NSP4 protein or synthetic peptide NSP4 114–135 is added exogenously to insect (6) or mammalian (8) cells.

A role for calcium in cytopathic effect (CPE) and cell death has been proposed for many pathological processes induced by virus (24). Increased $[Ca^{2+}]_i$ levels have been linked to cytotoxicity in MA104 cells (monkey kidney cells; Biowhittaker Inc., Walkersville, Md.) infected with group A rotaviruses (25). It has been proposed that NSP4-induced cytotoxicity is due to an increase in intracellular calcium levels in infected cells (5). NSP4 has been found to be cytotoxic to mammalian cells (5,11). NSP4 has also been shown to function as an enterotoxin causing diarrhea in young mice (7). Antibodies against NSP4 provide passive protection against rotavirus in the same animal model (7).

There is a need to develop alternative forms of NSP4 which have reduced cytotoxicity, but which retain a conformation which approximates that of the prototypic rotavirus strain, such that they are still antigenic and immunogenic. Such antigenic and immunogenic forms are candidates for inclusion in antigenic compositions to protect against rotavirus disease.

SUMMARY OF THE INVENTION

Accordingly, it in an object of this invention to identify regions of NSP4 which are responsible for cytotoxicity and increased intracellular calcium levels.

It is a further object of this invention to identify and develop develop alternative forms of NSP4 which have reduced cytotoxicity, but which are still antigenic and immunogenic, because they retain a conformation which approximates that of the prototypic rotavirus strain.

As described herein, there is a histidine at amino acid position 47 of NSP4 in the SA11 ATCC rotavirus strain (NSP4 (His)) compared to an asparagine in the Australia rotavirus strain derived by Holmes et al. and sequenced by Both et al. (NSP4 (Asn)). This substituted form, NSP4 (His), retains the major functions of NSP4 (Asn), i.e. cytotoxicity and intracellular calcium changes, but it is more cytotoxic to cells.

To produce an alternative form of NSP4 which has reduced toxicity, while retaining its antigenicity and immunogenicity, the histidine or asparagine at amino acid position 47 of NSP4 is mutagenized to another amino acid. For example, the codon CAT encoding the histidine or the codon AAT encoding the asparagine at amino acid 47 is mutagenized to GAA, which encodes aspartic acid. Other attenuating mutations of this amino acid may also be used to reduce the toxicity.

As also described herein, there is a lysine at amino acid position 48 in both the SA11 ATCC and Australian rotavirus strains. An alteration of the lysine to glutamic acid increases the intracellular calcium levels and the toxicity caused by the virus. Thus, amino acid 48 is also identified as a position which contributes to viral toxicity. To produce an alternative form of NSP4 which has reduced toxicity, while retaining its antigenicity and immunogenicity, the lysine at amino acid position 48 is mutagenized to another amino acid other than glutamic acid.

Amino acids flanking amino acid positions 47 and 48 may also be mutagenized in a similar manner. Still further mutations in other regions of NSP4 may also be combined with the mutations at amino acid positions 47 and/or 48.

As further described herein, this invention also relates to an isolated and purified nucleic acid sequence comprising a nucleic acid sequence encoding: (a) rotavirus NSP4 protein in which the histidine or asparagine at amino acid position 47 is mutagenized to another amino acid to produce an alternative form of NSP4 which has reduced toxicity, while retaining its antigenicity and immunogenicity; (b) rotavirus NSP4 protein in which the lysine at amino acid position 48 is mutagenized to another amino acid other than glutamic acid to produce an alternative form of NSP4 which has reduced toxicity, while retaining its antigenicity and immunogenicity; or (c) rotavirus NSP4 protein in which the histidine or asparagine at amino acid position 47 is mutagenized to another amino acid, and in which the lysine at amino acid position 48 is mutagenized to another amino acid other than glutamic acid, to produce an alternative form of NSP4 which has reduced toxicity, while retaining its antigenicity and immunogenicity.

This invention also relates to the construction of a plasmid which expresses an alternative form of NSP4 as described above.

In order to obtain expression of the alternative form of NSP4, the isolated and purified nucleic acid sequence is first inserted into a suitable plasmid vector. A suitable host cell is then transformed, transfected or infected with the plasmid. In an embodiment of this invention, the host cell is an Sf9 cell. The host cell is then cultured under conditions which permit the expression of said alternative form of NSP4 by the host cell.

In another embodiment of this invention, the alternative forms of NSP4 protein are used to prepare antigenic compositions which elicit a protective immune response against rotavirus in a mammalian host, or which ameliorate diarrheal symptoms in such a host which has been infected with rotavirus. The antigenic composition may further comprise an adjuvant, diluent or carrier. Examples of such adjuvants include aluminum hydroxide, aluminum phosphate, MPL™, Stimulon™ QS-21, IL-12 and cholera toxin. The antigenic compositions are administered to a mammalian host in an immunogenic amount sufficient to protect the host against disease caused by rotavirus or to ameliorate diarrheal symptoms in such a host which has been infected with rotavirus.

DETAILED DESCRIPTION OF THE INVENTION

Rotavirus SA11 was first isolated by Malherbe et al. in 1963 (2). The passage history of SA11 in Dr. Malherbe's laboratory is not available. The passage history for the virus used for the published sequence is not available. SA11 Clone 3 was provided by Dr. Estes with a passage history of 5.

Point mutations occur with regular frequency in RNA viruses. It has been estimated that rotavirus has a replication error frequency of $10^{-4}$ changes per nucleotide position per replication (26). Thus, individual isolates of the same virus are likely to have some nucleotide sequence differences. For example, two versions of VP7 in different clones of SA11 isolated from the same virus, with variations in glycosylation, have been reported (27). A single mutation in gene 9 of SA11 resulted in a nonglycosylated form of VP7 (clone 28). Therefore, the sequence of an individual cDNA clone of the virus or a single plasmid derived from an RT-PCR. amplification of viral RNA might not be a completely accurate representative of the viral consensus sequence.

As discussed in Example 2 below, gene 10 (also known as gene NS28) encoding NSP4 of SA11 rotavirus obtained from the American Type Culture Collection (ATCC accession number VR-899) was sequenced. A histidine at amino acid position 47 (NSP4 (His)) in this version of SA11's NSP4 was identified based on the nucleotide sequence, which was the sole amino acid difference from that of the previously published sequence of the Australian strain (12), which has an asparagine residue at this position (NSP4 (Asn)). It is believed that the sequence of SA11 gene 10 described herein, that is, the gene encoding NSP4 (His), is the prototypic sequence.

Although it is difficult to definitively conclude which is the true prototypic sequence of gene 10, because the passage history of SA11 rotavirus is not certain, it is believed that the sequence encoding NSP4 (His) is representative of the consensus because: i) it was observed in different passage numbers of the SA11 strain, including a very early passage (Lot 1N); ii) it was demonstrated by direct sequencing from both RT-PCR products (representative of the virus population) and individual clones; iii) it was also found in a different SA11 stock obtained from another laboratory (Estes) (clone 3); and iv) 43 of 44 published NSP4 sequences from different rotavirus strains have a His at the position 47.

Since most NSP4 studies (5–8,12,15–23) were based upon expression of the EDNA gene 10 clone from Both et al., it is important to know if NSP4 functions are fully conserved in the two NSP4 variants, that is, NSP4 (Asn) and NSP4 (His).

In order to assess whether the biological functions of the NSP4 protein are altered by the amino acid substitution of histidine for asparagine, the codon encoding histidine at position 47 was replaced with a codon encoding asparagine. A change at nucleotide 139 from A to C results in mutation from asparagine to histidine. Specifically, the codon (residues 139–141, where the start codon is residues 1–3) is changed from AAT to CAT. Both versions of the NSP4 genes were cloned into baculovirus transfer vectors and were then expressed insect cells.

The expression of NSP4 from Sf9 cells infected with recombinant baculovirus vectors was examined by western blot and SDS-PAGE. The synthesis of three forms of NSP4 in infected Sf9 cells (two glycosylated forms of 26 and 28 kilodaltons and one unglycosylated form of 20 kilodaltons) was detected with an NSP4 antipeptide antibody (see FIG. 5).

The expression of SA11 NSP4 in mammalian cells appears to be cytotoxic (5). Unusual morphologic changes have been observed in cells transfected with a plasmid expressing NSP4. Recently, Newton et al. have shown that the expression of NSP4 in mammalian cells infected with recombinant vaccinia virus resulted in killing of cells (11). It is demonstrated herein that NSP4 expression is also cytotoxic to insect (Sf9) cells. The expression of NSP4 in Sf9 cells infected with recombinant baculovirus resulted in significantly lower cell viability compared with cells expressing other rotaviral proteins, including VP2, VP4, VP6, and VP7.

As described in Example 3 below, expression of NSP4 (His) in insect cells induces the major cellular pathogenic effects associated with cytotoxicity. However, this single amino acid change significantly influenced the magnitude of the cytotoxic effects of SA11 NSP4. NSP4 (His) expressed in Sf9 cells resulted in significantly increased cell mortality as compared to that of NSP4 (Asn). Therefore, NSP4 (His) is more cytotoxic than NSP4 (Asn) when expressed in Sf9 cells. This result was confirmed as described in Example 7 below.

Recent data (5) showed that the expression of NSP4 in Sf9 cells results in a significant increase in intracellular calcium levels. It has been proposed (5,6) that the increased intracellular calcium might be responsible for pathogenesis caused by NSP4. As shown in Example 4 below, both NSP4 (His) and NSP4 (Asn) cause a significant increase in intracellular calcium levels. However, expression of NSP4 (His) results in even higher intracellular calcium levels than NSP4 (Asn). This result was confirmed as described in Example 8 below. The higher calcium levels observed in cells expressing NSP4 (His) are not due to overexpression of the protein, because a higher amount of NSP4 was expressed in Sf9 cells infected with recombinant baculovirus NSP4 (Asn) than in Sf9 cells infected with recombinant baculovirus NSP4 (His) (see Example 5 below). Therefore, a single amino acid change at position 47 significantly influences the function of NSP4 on the mobilization of intracellular calcium.

The functional NSP4 domain(s) responsible for cytopathology and toxicity have not been fully defined. However, the domain spanning amino acids 114 to 140 of NSP4 is known to be important for mobilizing intracellular calcium, as shown by: (i) A synthetic peptide corresponding to amino acids 114 to 135 of NSP4 functions similarly to intact protein in mobilizing intracellular calcium (6), and inducing diarrhea (7); and (ii) Zhang et al. reported that the virulent OSU virus differed from the avirulent form of this same virus by changes in amino acids 135, 136, 138 (9). However, other domains might also important for the function of NSP4. It has been shown that N-linked glycosylation (amino acids 8 and 18) of NSP4 might be required for removal of the transient envelope during viral morphogenesis (28). Recently, Newton et al. reported that the H3 domain (amino acids 55 to 85) is crucial for the cytotoxic and membrane destabilization activities of NSP4 (11). It is described herein that a single amino acid change (histidine to asparagine at position 47, which is adjacent to the H2 domain) significantly alters the function of NSP4. These results suggest that domains other than amino acids 114–140 are important for cytotoxicity and calcium mobilization of NSP4.

Figure 5:
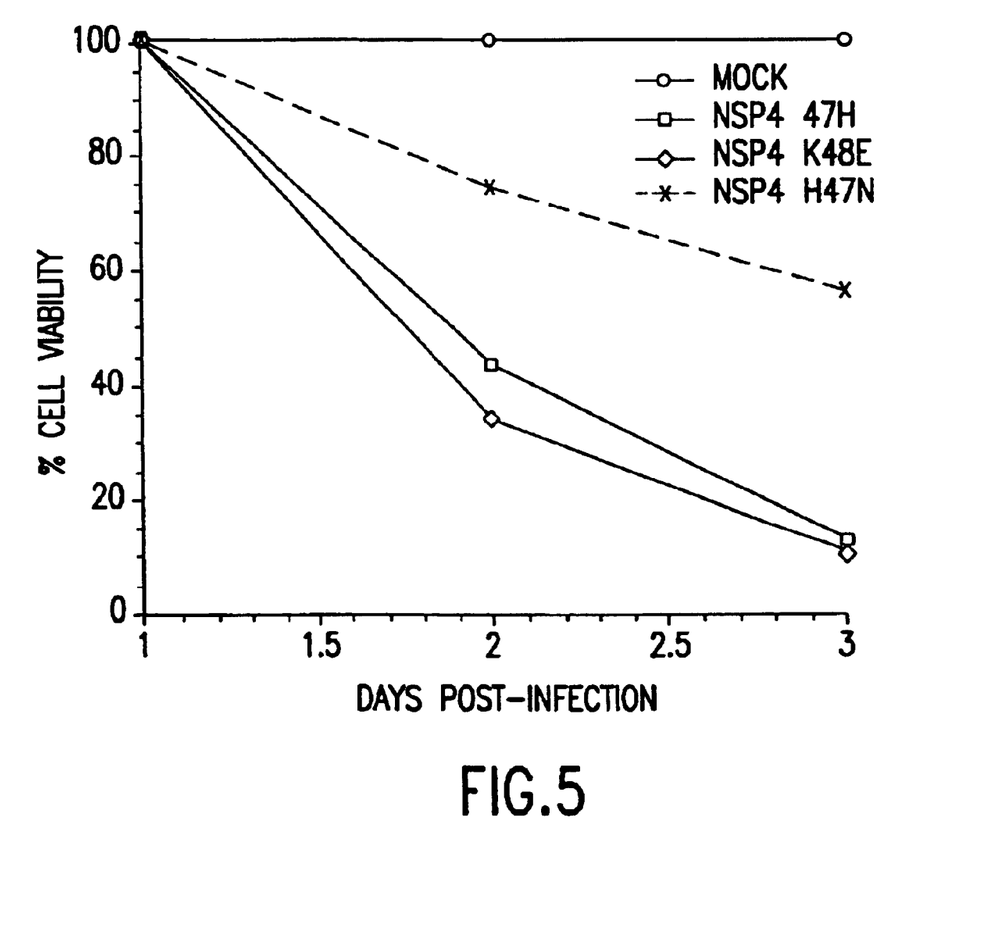
FIG. 5 depicts the cell viability of Sf9 cells infected with recombinant baculoviruses containing no rotavirus (mock infected) (circle), NSP 4 (His) at amino acid 47 (square), NSP4 (Asn) at amino acid 47 (cross), and NSP4 (Glu) at amino acid 48 (diamond). Sf9 cells were infected with recombinant baculoviruses at an MOI of 10. Cell viability was measured by trypan blue exclusion assay at the times indicated. The mean of each time point represents three independent infections.

NSP4 is an ER transmembrane protein (FIG. 5). A hydrophobicity analysis reveals three putative hydrophobic regions (H1–H3). The topology of NSP4 has been proposed in two models. Chan et al. proposed that the third hydrophobic domain (H3, amino acids 67 to 85) spans the ER membrane and that the second hydrophobic domain (H2, amino acids 28 to 47) resides in the lumen of the ER (15,27). Bergmann et al. suggested that the H2 domain (amino acids 30 to 54) traverses the ER membrane, while the H3 domain (amino acids 63 to 80) lies on the cytoplasmic side of the ER (20). In Bergmann's models, part of the H2 domain (amino acids 30 to 44) spans the ER membrane, while amino acid 47 (and amino acid 48) extends into the cytoplasmic site of the ER. Without being bound by the following, amino acid 47 (and amino acid 48) may be important for the interaction of NSP4 and ER membrane.

Changing the amino acid from asparagine (which is uncharged and polar) to histidine (which is basic and positively charged) at position 47 results in an alteration of charges in the H2 domain at physiological pH. Without being bound by the following, as a result of this charge alteration, NSP4 (His) may directly destabilize the ER membrane due to the additional charge or may indirectly damage the ER membrane by forming a structure with the C-terminal membrane destabilization domain of NSP4 (amino acids 114–140), thereby facilitating the membrane destabilization activity of NSP4 (18).

Thus, NSP4 (His) possesses the major functions of NSP4 (Asn) in pathogenesis (e.g. cytotoxicity and intracellular calcium changes). However, this single amino acid change at position 47 significantly affects the cytotoxicity of SA11 NSP4.

The histidine at amino acid position 47 of NSP4 is mutagenized by conventional recombinant DNA techniques to another amino acid to produce an alternative form of NSP4 which has reduced toxicity, while retaining its antigenicity and immunogenicity. For example, the codon CAT encoding the histidine or the codon AAT encoding the asparagine at amino acid 47 is mutagenized to GAA, which encodes aspartic acid.

Other attenuating mutations may also be used to reduce the toxicity of NSP4. Because of the limited number of possible amino acids at any given position, a person skilled in the art can readily construct a series of plasmids, each containing a different codon encoding a different amino acid at position 47. The resulting expressed NSP4 proteins are then readily tested in the cell viability and intracellular calcium level systems described herein in order to assess whether toxicity is reduced. Those alternative forms of NSP4 which result in reduced toxicity are then tested in a suckling (infant) mouse animal model system (7) to confirm that they have reduced toxicity. Alternative forms of NSP4 having reduced toxicity are then tested to confirm that they have retained antigenicity and immunogenicity as follows. Pregnant mice are immunized with an alternative form of NSP4. Suckling mice born to such immunized damn are then challenged with native NSP4 or whole rotavirus (29). Those suckling mice which do not develop diarrhea are thus passively protected by the acquired maternal antibodies generated by immunization of the dams with the alternative form of NSP4.

The residue at amino acid position 48 of NSP4 is also associated with toxicity. The Australian and SA11 rotavirus strains both have a lysine at amino acid position 48. When, as described in Examples 6–8 below, the lysine is mutagenized to glutamic acid by conventional recombinant DNA techniques, this alternative form has significant cytotoxicity and causes high intracellular calcium levels in Sf9 cells.

Therefore, in order to reduce the toxicity of NSP4, a person skilled in the art can again readily construct a series of plasmids, each containing a different codon encoding a different amino acid at position 48, other than glutamic acid. The resulting expressed NSP4 proteins are then readily tested in the cell viability and intracellular calcium level systems described herein in order to assess whether toxicity is reduced. Those alternative forms of NSP4 which result in reduced toxicity are then tested in the animal model systems described above to confirm that they have reduced toxicity, as well as retaining antigenicity and immunogenicity.

Alternative forms of NSP4 comprise those having a mutation at amino acid position 47, or having a mutation at amino acid position 48, or having mutations at both amino acid positions 47 and 48, as long as each alternative form has reduced toxicity, while retaining its antigenicity and immunogenicity.

In a further embodiment of this invention, amino acids flanking amino acid positions 47 and 48 may also be mutagenized in a similar manner. Still further mutations in other regions of NSP4 may also be combined with the mutations at amino acid positions 47 and/or 48.

As discussed above, Estes et al. have focused on the functional domain residing between amino acids 114–140 (30). However, as shown herein, other domains are important for the cytotoxicity of NSP4. The region within or near the H2 domain—specifically at amino acid 47 and/or at amino acid 48—is targeted to generate a genetically detoxified NSP4 protein. Mutations which introduce a proline in the H2 domain and/or H3 domain change the secondary/tertiary structure, and may thus decrease cytotoxic potential. These further mutations may be combined with those described above at amino acid 47.

These alternative forms of NSP4 have reduced cytotoxicity, but are still antigenic and immunogenic. Such detoxified antigenic and immunogenic forms are candidates for inclusion in antigenic compositions to protect against rotavirus disease.

This invention also relates to an isolated and purified nucleic acid sequence comprising a nucleic acid sequence encoding: (a) rotavirus NSP4 protein in which the histidine or asparagine at amino acid position 47 is mutagenized to another amino acid to produce an alternative form of NSP4 which has reduced toxicity, while retaining its antigenicity and immunogenicity; (b) rotavirus NSP4 protein in which the lysine at amino acid position 48 is mutagenized to another amino acid other than glutamic acid to produce an alternative form of NSP4 which has reduced toxicity, while retaining its antigenicity and immunogenicity; or (c) rotavirus NSP4 protein in which the histidine or asparagine at amino acid position 47 is mutagenized to another amino acid, and in which the lysine at amino acid position 48 is mutagenized to another amino acid other than glutamic acid, to produce an alternative form of NSP4 which has reduced toxicity, while retaining its antigenicity and imunogenicity.

A variety of host cell-vector systems are suitable for use to express the alternative forms of NSP4 described herein. The vector system is compatible with the host cell used. Suitable host cells include bacteria transformed with plasmid DNA, cosmid DNA or bacteriophage DNA; viruses such as vaccinia virus and adenovirus; yeast such as Pichia cells; insect cells such as Sf9 or Sf21 cells; or mammalian cell lines such as Chinese hamster ovary cells; as well as other conventional organisms. A variety of conventional transcriptional and translational elements can be used for the host cell-vector system.

The plasmid is introduced into the host cell by transformation, transduction, transfection or infection, depending on the host cell-vector system used. The host cell is then cultured under conditions which permit expression of an alternative form of NSP4 by the host cell.

The alternative forms of NSP4 protein are useful in the preparation of antigenic compositions to confer protection to a mammalian host against disease caused by rotavirus, or to ameliorate diarrheal symptoms in such a host which has been infected with rotavirus.

Antigenic compositions containing an alternative form of NSP4 protein may be mixed with immunologically acceptable diluents or carriers in a conventional manner to prepare injectable liquid Is solutions or suspensions. The level of antibodies elicited by the antigenic compositions may be improved by using certain adjuvants such as Stimulon™ QS-21 (Aquila Biopharmaceuticals, Inc., Framingham, Mass.), MPL™ (3-O-deacylated monophosphoryl lipid A; RIBI ImmunoChem Research, Inc., Hamilton, Mont.), aluminum phosphate, aluminum hydroxide, IL-12 (Genetics Institute, Cambridge, Mass.) and cholera toxin (either in a wild-type or mutant form, for example wherein the glutamic acid at amino acid position 29 is replaced by another amino acid, preferably a histidine, in accordance with U.S. Provisional Patent Application No. 60/102,430).

The antigenic compositions of this invention are administered by injection in a conventional manner, such as subcutaneous, intraperitoneal or intramuscular injection into mammals, as well as by oral, mucosal, intranasal or vaginal administration, to induce a protective immune response against disease caused by rotavirus or to ameliorate diarrheal symptoms in such a host which has been infected with rotavirus. The dosage to be administered is determined by means known to those skilled in the art. Protection or amelioration of symptoms may be conferred by a single dose of the antigenic composition, or may require the administration of several booster doses.

These alternative forms further are used as ligands to identify the as-yet unknown receptor for the rotavirus enterotoxin NSP4. They still further have therapeutic utility in treatment of gastrointestinal disease by forming a non-functional heterodimer to block the NSP4 receptor.

In order that this invention may be better understood, the following examples are set forth. The examples are for the purpose of illustration only and are not to be construed as limiting the scope of the invention.

EXAMPLES

Example 1

Cells, Viral Strains and Viral Infection

Cells and SA11 Rotaviruses

Figure 1:
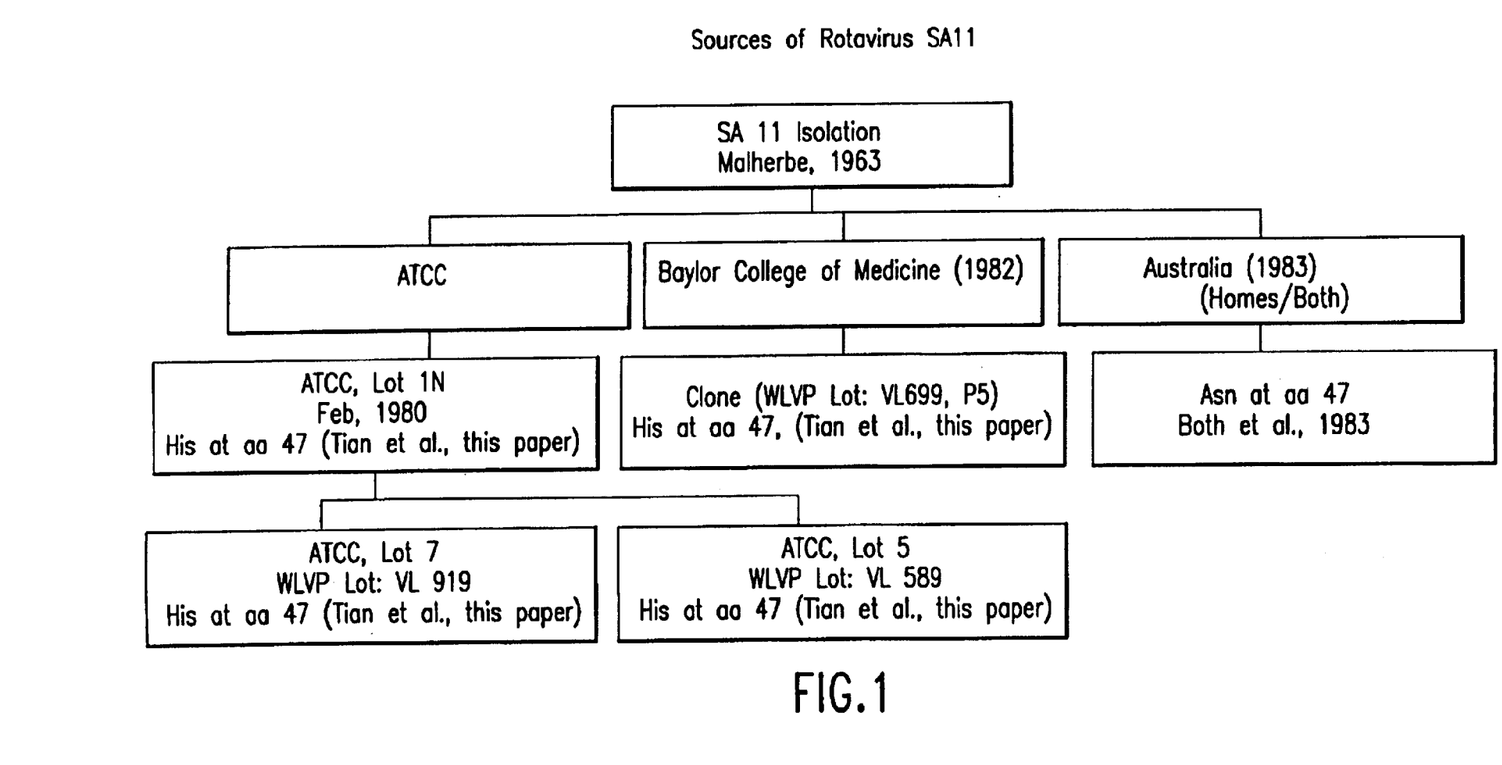
FIG. 1 depicts the sources of rotavirus SA11 virus stocks. The passage history of SA11 ATCC strain is indicated. WLVP represents Wyeth-Lederle Vaccines and Pediatrics, VL represents virus lot number used in WLVP.

The history of SA11 strains used in this study is shown in FIG. 1. SA11 rotavirus was obtained from the American Type Culture Collection. Lot 1N of SA11 rotavirus seed stock, which was an unpassaged viral stock originally submitted in 1980 (2), was a generous gift from Dr. Charles Buck (American Type Culture Collection, Manassas, Va.). The passage history of lot 1N is equivocal (with an unknown passage number in primary vervet monkey kidney and fetal rhesus monkey kidney cells). Lot 1N served as the virus seed at ATCC for Lots 2, 6, and 7 (Dr. Buck, personal communication). VL589 was purchased from ATCC (Lot 5). Lot 5 has an unknown passage number in primary vervet monkey kidney, and two passages in CV-1 cells. VL589 was passaged once in MA104 cells after receipt from ATCC. VL919 was also obtained from ATCC (Lot 7, with unknown passage number in primary vervet monkey kidney and fetal rhesus monkey kidney cells and five passages in MA104 cells). The SA11 clone 3 was kindly provided by Dr. Mary K. Estes, Baylor College of Medicine, with a passage number of five in MA104 cells.

Rotavirus Infection and Viral RNA Isolation

MA104 cells were grown and maintained in Modified Dulbecco's media with 10% fetal bovine serum. SA11 rotavirus was activated with L-1-tosylamide-2 phenylethyl chloromethyl ketone (TPCK) treated trypsin (Sigma) at a final concentration of 10 $\mu$g/mL for 30 minutes and added to MA104 cells at a multiplicity of infection (MOI) of 10. Messenger RNA was isolated from infected cells 10 hours post-infection using the Ultraspec RNA isolation system (Biotecx Laboratories, Inc., Houston Tex.).

Insect Cell Infections

Cells from the *Spodoptera frugiperda* insect cell line designated Sf9 (ATCC accession no. CAL 1711) were grown in serum-free SF 900 II (Gibco BRL, Gaithersburg, Md.) or Insect-Xpress (Biowhittaker Inc.) media, seeded at a density of 2.5×10$^5$/mL in 250 mL Erlenmeyer flasks on a gyrotory shaker at 120 rpm at 28° C. Cells were infected with recombinant baculovirus at a low MOI (0.2) at a density of 1.5×10$^6$/mL in a shaker flask. One milliliter of cell suspension was collected every 24 hours for cell viability studies (by trypan blue exclusion; see Example 3 below) and for western blot assays. Cells were grown in two well culture chambers (Nunc Inc., Naperville, Ill.) for imaging studies.

Example 2

RT/PCR and Sequencing

NSP4 cDNA synthesis from the purified viral messenger RNA (obtained in Example 1) was achieved using Ready to Go First-Strand Beads (Pharmacia Biotech Inc., Piscataway, N.J.), followed by PCR amplification. SA11 NSP4-specific primers used in the PCR reaction were based on the published NSP4 sequence (12). The 5' end of SA11 NSP4 specific primer was ATGGAAAAGCTTACCGACCTC (SEQ ID NO:1), and the 3' end of SA11 specific primer was CTCTTACATTGCTGCAGTC (SEQ ID NO:2). PCR products were sequenced directly using an ABI PRISM™ DNA Sequencing System (Perkin-Elmer Corporation, Forest City, Calif.). Alternatively, individual clones obtained from TA™ cloning reactions (Invitrogen, San Diego, Calif.) were sequenced. For sequencing the NSP4 gene in recombinant baculovirus, the viral DNA was extracted with phenol followed by ethanol precipitation. The NSP4 gene sequences were amplified by PCR using the NSP4-specific primers. The PCR products were purified using a Qiaquick™ Spin Kit (Qiagen, Santa Clarita, Calif.) and sequencing reactions were conducted using an ABI PRISM™ Dye Terminator Cycle Sequencing Ready Reaction Kit (Perkin-Elmer Corporation).

The gene 10 nucleotide sequences were obtained either by direct sequencing of the RT-PCR product from SA11 infected cells, or from clones of the RT-PCR products. A change at nucleotide 139 from A to C, such that the codon is changed from AAT to CAT, results in a difference at amino acid position 47 from asparagine to histidine. Specifically, it was found that the Australia strain derived by Holmes et al. and sequenced by Both et al. had an asparagine at amino acid position 47 of NSP4. In contrast, there is a histidine at amino acid position 47 of NSP4 in the SA11 ATCC strain.

In order to determine which version of NSP4 represents the authentic prototype, the nucleotide sequence of gene 10 was determined from other distinct SA11 virus stocks. Both the ATCC SA11 master seed virus from which all other SA11 stocks were derived, and an SA11 virus from a completely different source (Dr. Mary K. Estes, Baylor College of Medicine, Houston, Tex.), have a C at nucleotide position 139. Thus, most versions of NSP4 from different SA11 virus stocks have a histidine at amino acid position 47.

The sequences of NSP4 (His) and NSP4 (Asn) in recombinant baculovirus were reconfirmed by sequencing the PCR product from recombinant baculovirus extracts. The NSP4 (Asn) gene was constructed using the QuickChange™ Site-Directed Mutagenesis Kit (Stratagene, La Jolla, Calif.). Each of the NSP4 (His) and the NSP4 (Asn) genes was inserted into a copy of the pFastBac transfer vector (Life Technologies, Rockville, Md.). Recombinant baculoviruses were plaque purified three times and amplified at low MOI. The correct sequence for each virus was confirmed by the methods described above. The expression of NSP4 was confirmed by inmmunofluororescent staining of Sf9 cells infected with the recombinant baculoviruses and by western analysis using a NSP4 antipeptide antibody (18; see also Example 4 below).

Example 3

Cell Viability Measurements

Sf9 cells were seeded at a density of 2.5×10$^5$/mL in 250 mL Erlemmeyer flasks in serum-free Sf-900 II SFM™ media or Insect-Xpress media and infected with recombinant baculovirus at a MOI of 0.2 when the cell density reached 1.5×10$^6$/mL. Cells were grown in a gyrotory shaker at 28° C. at a speed of 120 rpm. Cell viability was determined by the trypan blue exclusion assay (11). Briefly, an aliquot of the cell suspension (50 $\mu$L) was incubated with an equal amount of 2% trypan blue for five minutes; stained and unstained cells were then counted.

The viability of Sf9 cells expressing various rotaviral proteins was measured on a daily basis over six days (D1 through D6) and the results shown in Table 1. Data are presented as mean +/− standard deviation from at least three independent experiments. Recombinant baculovirus expressing VP2, VP4, VP6 and VP7 was kindly provided by Dr. Mary K. Estes (Baylor College of Medicine, Houston, Tex.).

TABLE 1

| | \multicolumn{6}{c|}{Cell Viability (%)} |
|---|---|---|---|---|---|---|
| | VP2 | VP4 | VP6 | VP7 | NSP4 (His) | NSP4 (Asn) |
| D1 | 99.5 +/− 0.87 | 96.9 +/− 0.56 | 98.1 +/− 0.9 | 98 +/− 1.2 | 95.4 +/− 1.99 | 97.6 +/− 1 |
| D2 | 96.8 +/− 1.23 | 97.5 +/− 1.8 | 97.5 +/− 0.7 | 96.3 +/− 0.8 | 65.9 +/− 2 | 83 +/− 1.6 |
| D3 | 94.3 +/− 1.87 | 90.2 +/− 1.5 | 88.1 +/− 7 | 80.7 +/− 3.2 | 47.2 +/− 0.5 | 61.6 +/− 0.3 |
| D4 | 81 +/− 2.6 | 73 +/− 1.7 | 61 +/− 3.5 | 43 +/− 7 | 21 +/− 1.4 | 36.4 +/− 2.9 |
| D5 | 57 +/− 4 | 31 +/− 4 | 22.5 +/− 6.8 | 12 +/− 5.2 | 3.9 +/− 1 | 10.8 +/− 4.7 |
| D6 | 38 +/− 9 | 11 +/− 6 | 7.5 +/− 2.4 | 3 +/− 1.4 | 0 | 0 |

Figure 2:
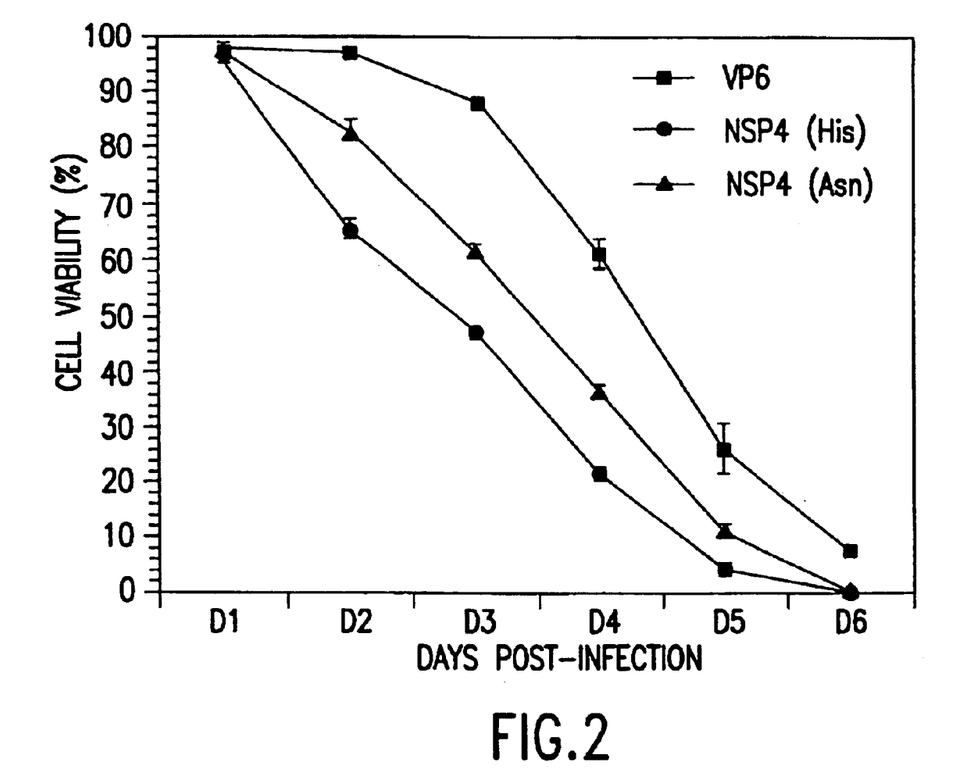
FIG. 2 depicts the cell viability of Sf9 cells infected with recombinant baculoviruses containing the rotavirus genes VP6 (square), NSP4 (His) at amino acid 47 (circle) and NSP4 (Asn) at amino acid 47 (triangle), respectively, at a MOI of 0.2. Cell viability was measured by trypan blue exclusion assay at times indicated. The mean of each time point represents three independent infections.

The expression of NSP4 is cytotoxic to Sf9 cells. As seen in Table 1, NSP4 (His) killed cells more rapidly than NSP4 (Asn), while the expression of other rotavirus proteins, including VP2, VP4, VP6 and VP7, did not result in cell death until a very late stage of infection. However, expression of NSP4 resulted in rapid cell death. Viability 48 hours post-infection (D2) was 96.8%, 97.5%. 97.5%, and 96.3% for cells expressing VP2, VP4, VP6, and VP7, respectively, while viability was 65.9% and 83% for cells expressing NSP4 (His) and NSP4 (Asn), respectively. Thus, NSP4 (His) has a more profound effect on cellular toxicity than NSP4 (Asn). Sf9 cells expressing NSP4 (His) were killed much more rapidly than Sf9 cells expressing NSP4 (Asn). At seventy-two hours post infection (D3), cell viability was 94.3, 90.2, 88.1, and 80.7% for cells expressing VP2, VP4, VP6, and VP7 respectively. Cell viability was 47.2 and 61.6% for cells expressing NSP4 (His) and NSP4 (Asn), respectively (Table 1 and FIG. 2). There was no statistically significant difference in cell viability among cells expressing VP2, VP4, VP6 and VP7 at any time point. However, there was a significant difference in viability between cells expressing the different versions of NSP4, in addition to significant differences in viability between cells expressing either version of NSP4 and those cells expressing the other rotaviral proteins, at both 48 and 72 hours post-infection (p<0.05). NSP4 (His) is more cytotoxic to Sf9 cells than NSP4 (Asn).

Example 4

Measurement of Intracellular Calcium Levels $[Ca^{2+}]_i$ was determined using the fluorescent $Ca^{2+}$ indicator Fura-2/AM, measured with a Nikon Diaphot™ fluorescence microscope equipped with a Quantex™ QX-7 CCD camera and digital imaging system (31). Briefly, Sf9 cells were loaded with Fura-2/AM (Molecular Probes, Eugene, Oreg.) at a final concentration of 2 µM for 30 minutes at room temperature. The intracellular calcium levels in individual cells were calculated as described by Grynkiewicz et al. (32) and Nankova et al. (31) and expressed as a ratio of absorbance measured at 340 and 380 nm. The binding of calcium shifts the absorbence spectrum of fura-2 to the shorter wavelength (from 380 to 340 nm). The absorbance ratio of 340/380 represents the level of free intracellular calcium. For each experiment, 10 images were taken. Intracellular calcium concentrations were calculated from twelve cells in each image. At least three independent experiments were performed.

Figure 3A:
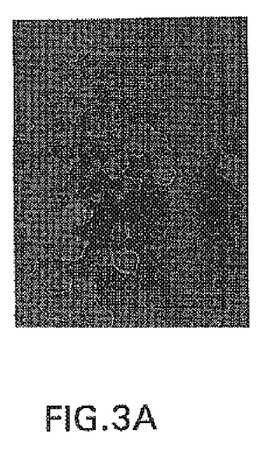
FIG. 3 depicts intracellular calcium levels in Sf9 cells (mock infected) (left panel), Sf9 cells expressing NSP4 (Asn) at amino acid 47 (middle panel), and Sf9 cells expressing NSP4 (His) at amino acid 47 (right panel). Images were taken from a representative experiment illustrating [Ca2+]i ratio (340/380 nm).
Figure 3B:
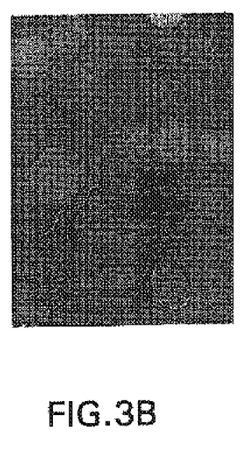
Figure 3C:
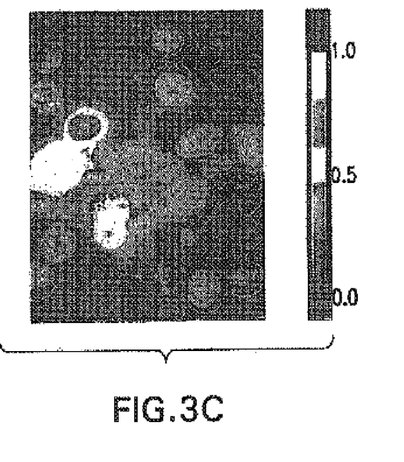

It has been shown that NSP4 expression in Sf9 cells resulted in a significant increase in intracellular calcium levels (5). It has been proposed that increases in intracellular calcium caused the SA11-mediated cytotoxicity of mammalian cells (25). The same contention has been advanced for Sf9 cells expressing NSP4 (15). The intracellular calcium levels in Sf9 cells expressing NSP4 (His) and NSP4 (Asn) were measured. The results depicted in FIG. 3 demonstrate that significantly higher intracellular calcium levels were observed in Sf9 cells expressing NSP4 (His) (right panel) than Sf9 cells expressing NSP4 (Asn) (center panel). At 48 hours after infection, the intracellular calcium levels in mock infected Sf9 cells, Sf9 cells expressing NSP4 (Asn) and Sf9 cells expressing NSP4 (His) were 0.12, 0.32, and 0.48 (ratio of 340/380 nm readings following Fura-2/AM addition), respectively. This corresponds to the following intracellular calcium concentrations: 80 nM for mock infected Sf9 cells, 213 nM for NSP4 (Asn) expressing cells and 320 nM for NSP4 (His) expressing cells. Thus, the expression of NSP4 (Asn) caused a significant increase in intracellular calcium levels as reported previously (5). However, there was a significantly higher intracellular calcium level in cells expressing NSP4 (His) compared to cells expressing NSP4 (Asn) (P<0.05).

Example 5

Western Blot Analysis

Although both versions of the gene encoding NSP4 were cloned separately into copies of the same baculovirus transfer vector, it is possible that the protein expression levels are different for the two recombinant baculoviruses expressing the two version of NSP4. To rule out the possibility that the increased toxicity and intracellular calcium accumulation associated with NSP4 (His) expression are due to the difference in protein expression levels between the two forms, the absolute amounts of NSP4 in Sf9 cells were measured. Sf9 cells were infected with recombinant baculovirus at a MOI of 0.2 and harvested at 48 hours post-infection. Equal amounts of sample (lysates from $2 \times 10^4$ cells) were loaded on SDS-PAGE and detected by western analysis using an NSP4 antipeptide antibody (FIG. 4).

This NSP4 antipeptide antibody was prepared in two Elite-New Rabbits by Covance Research Products Inc. (Denver, Pa.). Briefly, a synthetic peptide with a sequence of Cys Asp Lys Leu Thr Thr Arg Glu Ile Glu Gln Val Glu Leu Leu Lys Arg Ile Tyr Lys Asp Leu Thr (SEQ ID NO:3) was synthesized and crosslinked with KLH. The N-terminal added cysteine was used to facilitate specific crosslinking. The rest of the sequence represents residues 114–135 of NSP4. Five hundred µg of crosslinked peptide and 500 µL of FCA was mixed and injected intradermally. Rabbits were boosted with 250 µg of crosslinked peptide mixed with 250 µL IFA four times at three week intervals.

Equal aliquots of a sample from baculovirus recombinant-infected Sf9 cells harvested 48 hours post-infection were analyzed by SDS-PAGE. The separated proteins were electroblotted onto nitrocellulose membranes, which were then blocked with PBS containing 5% BLOTTO (Bio-Rad, Inc., Hercules, Calif.) for 30 minutes at room temperature and incubated for one hour at room temperature with a 1:100 dilution of NSP4-specific antipeptide antibody in PBS. After three washes in PBS, horseradish peroxidase (HRP)-conjugated goat anti-rabbit immunoglobulin (1:200 dilution) was added to the membrane and incubated for one hour, followed by color development with an HRP™ Substrate Kit (Bio-Rad, Inc.).

Figure 4:
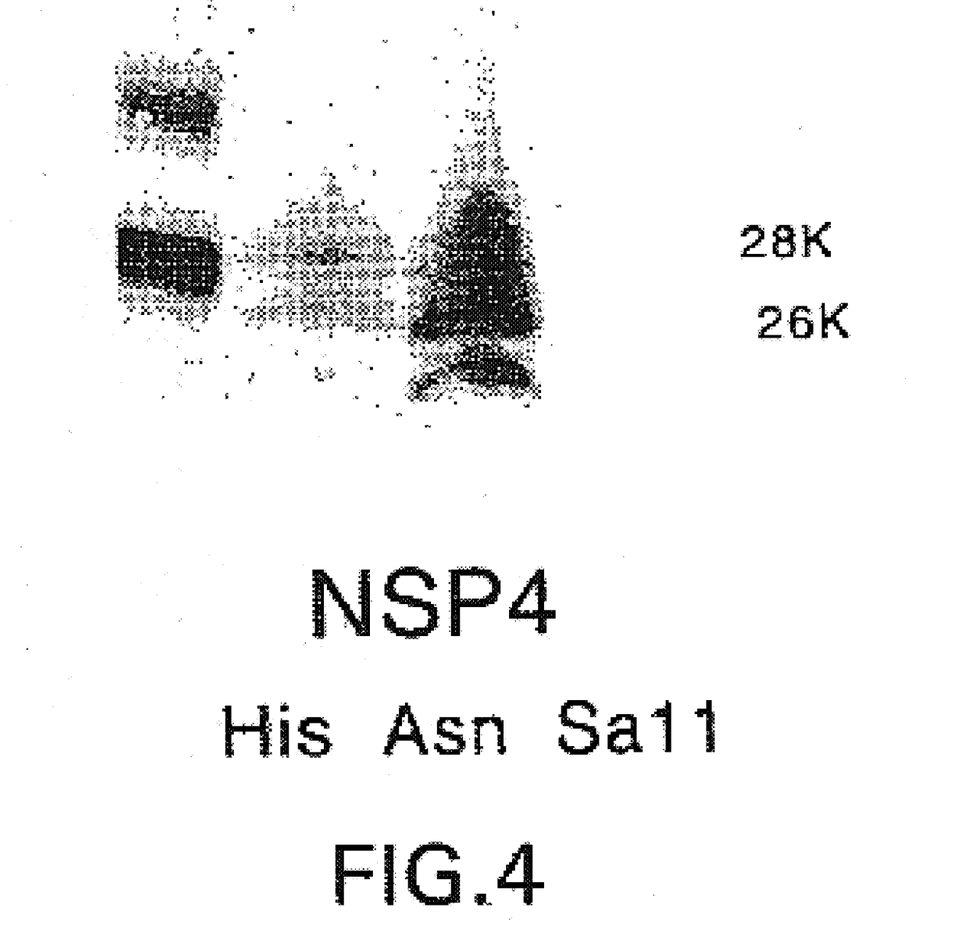
FIG. 4 depicts the western blot analysis of expression of NSP4s in Sf9 cells: Lane 1—NSP4 (His) at amino acid 47; Lane 2—NSP4 (Asn) at amino acid 47; Lane 3—SA11 infected MA104 cell lysate as positive control; Lane 4—molecular weight markers.

As shown in FIG. 4, more NSP4 was expressed in Sf9 cells infected with recombinant baculovirus expressing NSP4 (Asn) (lane 3) than in cells expressing NSP4 (His) (lane 2), as measured by the intensity of bands representing glycosylated and nonglycosylated NSP4. Essentially identical results were obtained when equivalent amounts of recombinant baculovirus infected total cell protein were compared by western analysis. The expression of NSP4 was detected as early as 24 hours and reached a peak between 48 hours and 72 hours. Degradation of NSP4 was observed after 72 hours post-infection. At each time point, except at 24 hours post-infection, the expression of NSP4 (Asn) was higher than the expression of NSP4 (His). Therefore, the cytotoxicity of the NSP4 (His) is not due to higher levels of expression of NSP4 (His) compared to NSP4 (Asn).

Results from at least three independent experiments for cell viability and calcium concentration determination were analyzed by Bonferroni's (multiple comparison) t-test. Briefly, this method performs a paramatric analysis of variance, followed by the pairwise comparisons with t-tests. The P values were multiplied by the number of comparisons that were made to account for the compounding risk of doing many statistical comparisons (33).

Example 6

Expression of NSP4 Protein From Sf9 Cells Infected with Recombinant Baculovirus

The gene encoding the NSP4 protein (His) was inserted into the pFastBac baculovirus-based transfer plasmid (Gibco BRL, Gaithersburg, Md.). This plasmid was mutated by replacing an A with a G at nucleotide 142. This mutation changed the codon from AAA (lysine) to GAA (glutamic acid). A third recombinant was generated by inserting the gene encoding the NSP4 protein (Asn) into the pFastBac transfer plasmid. Each plasmid was transfected into E. coli DH10Bac competent cells (Gibco BRL). White colonies were selected that contained the recombinant baculovirus DNA. Recombinant baculovirus DNA was then purified. Sf9 cells were separately transfected with these three recombinant baculovirus DNAs, and recombinant baculoviruses were plaque purified as described (34). The sequences of the three NSP4 genes were confirmed. These constructs were used in Examples 7 and 8 below.

Example 7

Further Cell Viability Measurements

The protocol of Example 3 was followed, except that an MOI of 10 was used and three recombinant forms of NSP4 protein were evaluated: NSP4 (Asn) at amino acid 47, NSP (His) at amino acid 47 and NSP (His) at amino acid 47, (Glu) at amino acid. 48. The mean of each time point represents three independent infections.

The expression of NSP4 is cytotoxic to Sf9 cells. As seen in FIG. 5, NSP (His) at amino acid 47, (Glu) at amino acid 48 killed cells slightly more rapidly than NSP4 (His) at amino acid 47, while both of these forms killed cells at a statistically significantly higher rate than NSP4 (Ann) at amino acid 47, based on Dunnett's multiple comparison test. These results indicate that NSP (His) at amino acid 47, (Glu) at amino acid 48 is the most toxic, while NSP4 (Asn) is the least toxic of the three forms to cells.

Example 8

Further Measurement of Intracellular Calcium Levels

Figure 6:
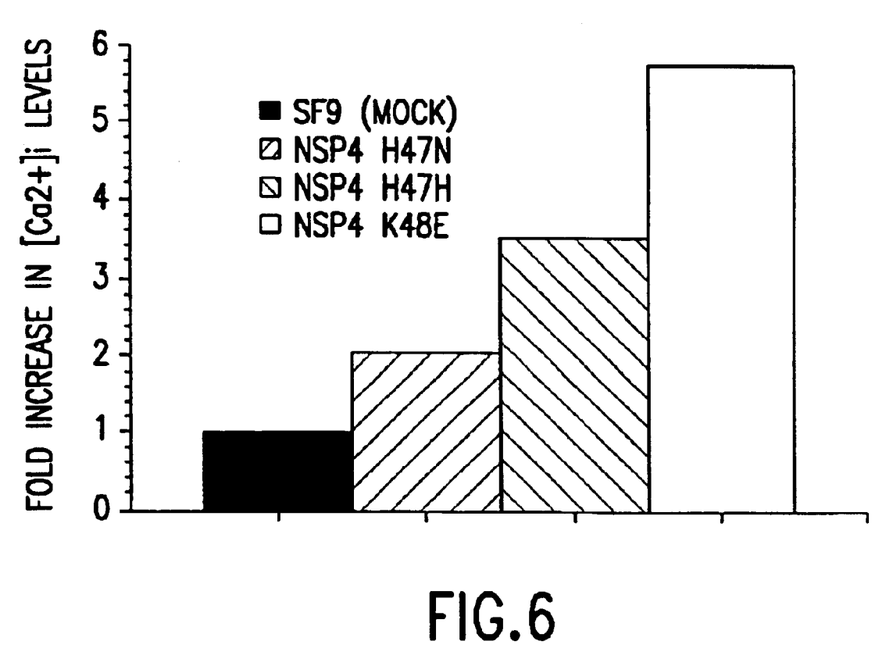
FIG. 6 depicts intracellular calcium levels in Sf9 cells (mock infected) (black bar), and Sf9 cells expressing NSP4 (Asn) at amino acid 47 (dark grey bar), NSP 4 (His) at amino acid 47 (light grey bar), and NSP4 (Glu) at amino acid 48 (white bar), respectively. Sf9 cells were infected with recombinant baculovirus at an MOI of 10. Intracellular calcium was measured at 48 hours post infection using the fluorescent calcium indicator fura-2. Each column shows the intracellular calcium levels relative to mock infected Sf9 cells. Each column represents the mean of three experiments.

The protocol of Example 4 was followed, except that three recombinant forms of NSP4 protein were evaluated: NSP4 (Asn) at amino acid 47, NSP (His) at amino acid 47 and NSP (His) at amino acid 47, (Glu) at amino acid 48. The results are shown in FIG. 6. The bars show the intracellular calcium levels of Sf9 cells infected with the three NSP4 recombinants and mock infected Sf9 cells. Each bar represents the mean of three experiments.

The highest intracellular calcium levels were observed in cells expressing NSP (His) at amino acid 47, (Glu) at amino acid 48, followed by NSP4 (His) and then NSP4 (Asn). These results indicate that NSP (His) at amino acid 47, (Glu) at amino acid 48 has the most profound effect on intracellular calcium levels, while NSP4 (Asn) has the least effect of the three forms. The differences were statistically significant according to Dunnett's multiple comparison test.

Bibliography

1. Kapikian, A. Z. and Chanock, R. M., pages 1657–1709 of Volume 2, *Fields Virology*, B. N. Fields, et al., Eds. (3rd ed., Raven Press, 1996).
2. Malherbe, H. E., et al., *S. Afr. Med. J.*, 37, 401–411 (1963).
3. Dyall-Smith, M. L., and Holmes, I. H., *J. Virol.*, 38, 1099–1103 (1980).
4. Estes, M. K., at al., *J. Virol.*, 61, 1488–1494 (1987).
5. Tian, P., et al., *J. Virol.*, 68, 251–257 (1994).
6. Tian, P., et al., *J. Virol.*, 69, 5763–5772 (1995).
7. Ball J., et al., *Science*, 272, 101–104 (1996).
8. Dong, Y., et al., *Proc. Nat'l Acad. Sci., USA*, 94, 3960–3965 (1997).
9. Zhang, M., et al., *J. Virol.*, 172, 3666–3672 (1998).
10. Hoshino, Y., et al., *Virology*, 209, 274–280 (1995).
11. Newton, K., et al., *J. Virol.*, 71, 9458–9465 (1997).
12. Both, G. W., et al., *J. Virol.*, 48, 335–339 (1983).
13. Sanger, F., et al., *Proc. Nat'l Acad. Sci., USA*, 5463–5467 (1977).
14. Maxam, A. M., and Gilbert, W., *Proc. Nat'l Acad. Sci., USA*, 74, 560–564 (1977).
15. Chan, W. K., et al., *Virology*, 164, 435–444 (1988).
16. Au, K. -S., et al., *J. Virol.*, 63, 4553–4562 (1989).
17. Au, K. -S., et al., *Virology*, 194, 665–673 (1993).
18. Tian, P., et al., *J. Virol.*, 70, 6973–6978 (1996).
19. Boyle D. B., et al., *Gene*, 35, 169–177 (1985).
20. Bergmann, C. C., et al., *EMBO J.*, 8, 1695–1703 (1989).
21. Meyer, J. C., et al., *Virology*, 171, 98–107 (1989).
22. Taylor, J. A., *Virology*, 194, 807–814 (1993).
23. Taylor, J. A., et al., *EMBO J.*, 15, 4469–4476 (1996).
24. Nicotera, P., et al., *Toxicol.*, 32, 449470 (1992).
25. Michelangeli, F., et al., *Virology*, 181, 520–527 (1991).
26. Blackhall, J., et al., *Virology*, 225, 181–190 (1996).
27. Chan, W. K., et al., *Virology*, 151, 243–252 (1986).
28. Petrie, B. L., et al., *J. Virol.*, 46, 270–274 (1983).
29. Sheridan, J. F., et al., *J. Inf. Dis.*, 149, 434–438 (1984).
30. Published International Application No. WO 97/00099.
31. Nankova, B, et al., *Mol. Brain Res.*, 35, 164–172 (1996).
32. Grynkiewicz, G., et al., *J. Biol. Chem.*, 260, 3440–3450 (1985).

33. Wason, C. J., et al., pages 499–502 of *Statistics for management and economics* (5th ed, Allyn and Bacon, Boston, Mass., 1993).
34. Luckow, V. A., et al., *J. Virol.*, 67, 4566–4579 (1993).

What is claimed is:

1. A rotavirus nonstructural protein 4 (NSP4) in which the histidine or asparagine at amino acid position 47 is mutagenized to aspartic acid to produce an alternative form of NSP4 which has reduced toxicity, while retaining its antigenicity and immunogenicity.

2. A rotavirus NSP4 in which the histidine or asparagine at amino acid position 47 is mutagenized to another amino acid, and in which the lysine at amino acid position 48 is mutagenized to another amino acid other than glutamic acid, to produce an alternative form of NSP4 which has reduced toxicity, while retaining its antigenicity and immunogenicity.

3. The rotavirus NSP4 of claim 2 where the amino acid at position 47 is aspartic acid.

4. The rotavirus NSP4 of claim 2 which further comprises at least one mutation in a region of NSP4 other than at amino acids 47 and 48 to produce an alternative form of NSP4 which has reduced toxicity, while retaining its antigenicity and immunogenicity.

5. An antigenic composition comprising a rotavirus NSP4 in which the histidine or asparagine at amino acid position 47 is mutagenized to aspartic acid to produce an alternative form of NSP4 which has reduced toxicity, while retaining its antigenicity and immunogenicity.

6. The antigenic composition of claim 5, which further comprises an adjuvant, diluent or carrier.

7. An antigenic composition comprising a rotavirus NSP4 in which the lysine at amino acid position 48 is mutagenized to another amino acid other than glutamic acid to produce an alternative form of NSP4 which has reduced toxicity, while retaining its antigenicity and immunogenicity, which further comprises an adjuvant, diluent or carrier.

8. An antigenic composition comprising a rotavirus NSP4 in which the histidine or asparagine at amino acid position 47 is mutagenized to another amino acid, and in which the lysine at amino acid position 48 is mutagenized to another amino acid other than glutamic acid, to produce an alternative form of NSP4 which has reduced toxicity, while retaining its antigenicity and immunogenicity.

9. The antigenic composition of claim 8 where the amino acid at position 47 is aspartic acid.

10. The antigenic composition of claim 8 which further comprises at least one mutation in a region of NSP4 other than at amino acids 47 and 48 to produce an alternative form of NSP4 which has reduced toxicity, while retaining its antigenicity and immunogenicity.

11. The antigenic composition of claim 8 which further comprises an adjuvant, diluent or carrier.

12. An isolated and purified nucleic acid sequence which comprises a nucleic acid sequence encoding rotavirus NSP4 in which the histidine or asparagine at amino acid position 47 is mutagenized to another amino acid, and in which the lysine at amino acid position 48 is mutagenized to another amino acid other than glutamic acid, to produce an alternative form of NSP4 which has reduced toxicity, while retaining its antigenicity and immunogenicity.

13. A plasmid containing an isolated and purified nucleic acid sequence which comprises a nucleic acid sequence encoding rotavirus NSP4 in which the histidine or asparagine at amino acid position 47 is mutagenized to another amino acid, and in which the lysine at amino acid position 48 is mutagenized to another amino acid other than glutamic acid, to produce an alternative form of NSP4 which has reduced toxicity, while retaining its antigenicity and immunogenicity.

14. A host cell transformed, transfected or infected with the plasmid of claim 13.

15. A method of producing an alternative form of rotavirus NSP4 which comprises transforming, transfecting or infecting a host cell with a plasmid and culturing the host cell under conditions which permit the expression of said rotavirus NSP4 by the host cell, wherein said plasmid contains an isolated and purified nucleic acid sequence which comprises a nucleic acid sequence encoding rotavirus NSP4 in which the histidine or asparagine at amino acid position 47 is mutagenized to another amino acid to produce an alternative form of NSP4 which has reduced toxicity, while retaining its antigenicity and immunogenicity.

16. A method of producing an alternative form of rotavirus NSP4 which comprises transforming, transfecting or infecting a host cell with a plasmid and culturing the host cell under conditions which permit the expression of said rotavirus NSP4 by the host cell, whereas said plasmid contains an isolated and purified nucleic acid sequence which comprises a nucleic acid sequence encoding rotavirus NSP4 in which the lysine at amino acid position 48 is mutagenized to another amino acid other than has glutamic acid to produce an alternative form of NSP4 has reduced toxicity, while retaining its antigenicity and immunogenicity.

17. A method of producing an alternative form of rotavirus NSP4 which comprises transforming, transfecting or infecting a host cell with the plasmid of claim 13 and culturing the host cell under conditions which permit the expression of said rotavirus NSP4 by the host cell.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Rotavirus

<400> SEQUENCE: 1
atggaaaagc ttaccgacct c                                              21

<210> SEQ ID NO 2
<211> LENGTH: 19
<212> TYPE: DNA
<213> ORGANISM: Rotavirus

<400> SEQUENCE: 2
ctcttacatt gctgcagtc                                                 19

<210> SEQ ID NO 3
<211> LENGTH: 23
<212> TYPE: PRT
<213> ORGANISM: Artificial Sequence
<220> FEATURE:
<221> NAME/KEY:
<222> LOCATION:
<223> OTHER INFORMATION: First amino acid cysteine is provided to
      facilitate cross-linking; remaining amino acids represent
      amino acids 114-135 of rotavirus NSP4 protein

<400> SEQUENCE: 3

Cys Asp Lys Leu Thr Thr Arg Glu Ile Glu Gln Val Glu Leu Leu Lys
 1               5                  10                  15

Arg Ile Tyr Lys Asp Leu Thr
            20
```